United States Patent
Bartels et al.

(10) Patent No.: US 12,037,539 B2
(45) Date of Patent: Jul. 16, 2024

(54) ALKYL LACTONE-DERIVED HYDROXYAMIDES AND ALKYL LACTONE-DERIVED HYDROXYESTERS FOR THE CONTROL OF NATURAL GAS HYDRATES

(71) Applicant: ChampionX LLC, Sugar Land, TX (US)

(72) Inventors: Jeremy Wayne Bartels, Sugar Land, TX (US); Jeffrey M. Servesko, Bend, OR (US)

(73) Assignee: ChampionX LLC, Sugar Land, TX (US)

( * ) Notice: Subject to any disclaimer, the term of this patent is extended or adjusted under 35 U.S.C. 154(b) by 84 days.

(21) Appl. No.: 17/861,360

(22) Filed: Jul. 11, 2022

(65) Prior Publication Data
US 2022/0363976 A1    Nov. 17, 2022

Related U.S. Application Data

(63) Continuation of application No. 16/507,873, filed on Jul. 10, 2019, now Pat. No. 11,414,588.
(Continued)

(51) Int. Cl.
*C09K 8/524*    (2006.01)
*C07C 237/10*    (2006.01)
(Continued)

(52) U.S. Cl.
CPC ............ *C09K 8/524* (2013.01); *C07C 237/10* (2013.01); *C07D 223/04* (2013.01); *C09K 8/52* (2013.01); *C09K 2208/22* (2013.01)

(58) Field of Classification Search
CPC ...... C09K 8/52; C09K 8/524; C09K 2208/22; C07C 237/10
See application file for complete search history.

(56) References Cited

U.S. PATENT DOCUMENTS 2,923,738 A    2/1960  Williams et al.
3,062,631 A    11/1962 Thompson
(Continued)

FOREIGN PATENT DOCUMENTS

CA    1240669 A    8/1988
CN    105022237 A    11/2015
(Continued)

OTHER PUBLICATIONS

Tebbji et al. (2007) "The effect of some lactones as inhibitors for the corrosion of mild steel in 1 M hydrochloric acid", Materials Chemistry and Physics, vol. 106, Issue 2-3, pp. 260-267.
(Continued)

*Primary Examiner* — Aiqun Li
(74) *Attorney, Agent, or Firm* — Scheef & Stone, LLP; Keith C. Rawlins

(57) ABSTRACT

Disclosed are alkyl lactone-derived hydroxyamides and alkyl lactone-derived hydroxyesters used in compositions and methods for inhibiting natural gas hydrate agglomerates. The alkyl lactone-derived hydroxyamides and alkyl lactone-derived hydroxyesters are reaction products of an alkyl lactone and an amine, and an alkyl lactone and an alcohol, respectively.

7 Claims, 5 Drawing Sheets

Related U.S. Application Data

(60) Provisional application No. 62/697,153, filed on Jul. 12, 2018.

(51) Int. Cl.
    *C07D 223/04*     (2006.01)
    *C09K 8/52*     (2006.01)

(56) References Cited

U.S. PATENT DOCUMENTS

| | | |
|---|---|---|
| 3,436,463 A | 4/1969 | Mayhew et al. |
| 3,831,678 A | 8/1974 | Mondshine |
| 3,832,367 A | 8/1974 | Heiba et al. |
| 3,989,637 A | 11/1976 | Hogue et al. |
| 4,148,926 A * | 4/1979 | Baker ............... C07D 307/68 426/321 |
| 4,167,514 A | 9/1979 | Brois et al. |
| 4,179,392 A | 12/1979 | Heiba et al. |
| 4,263,014 A | 4/1981 | Davis et al. |
| 4,828,740 A | 5/1989 | Farng et al. |
| 4,866,142 A | 9/1989 | Gutierrez et al. |
| 4,963,275 A | 10/1990 | Gutierrez et al. |
| 5,055,230 A | 10/1991 | Clubley et al. |
| 5,237,090 A | 8/1993 | Swarup et al. |
| 6,054,514 A | 4/2000 | Kulkarni |
| 6,368,552 B1 | 4/2002 | Shimura et al. |
| 6,583,213 B1 | 6/2003 | Fawkes et al. |
| 7,105,628 B2 | 9/2006 | Kuntimaddi et al. |
| 8,859,675 B2 | 10/2014 | Richards et al. |
| 2004/0127608 A1 | 7/2004 | Pardoen et al. |
| 2010/0041857 A1 | 2/2010 | Harris et al. |
| 2010/0069541 A1 | 3/2010 | Thetford et al. |
| 2015/0299628 A1 | 10/2015 | Choi et al. |
| 2016/0122619 A1 | 5/2016 | Lucente-Schultz et al. |
| 2017/0009101 A1 | 1/2017 | Yasui |
| 2017/0260409 A1 | 9/2017 | Thetford et al. |
| 2017/0306504 A1 | 10/2017 | Moloney |
| 2020/0017754 A1 | 1/2020 | Moloney et al. |

FOREIGN PATENT DOCUMENTS

| | | |
|---|---|---|
| CN | 106046868 A | 10/2016 |
| EP | 0491538 A1 | 6/1992 |
| FR | 1224810 A | 6/1960 |
| GB | 1095659 A | 12/1967 |
| GB | 1520599 A | 8/1978 |
| JP | 2013129933 A | 7/2013 |
| KR | 101830944 B1 | 2/2018 |
| RU | 2217428 C2 | 11/2003 |
| WO | 03054120 A1 | 7/2003 |
| WO | 2016180916 A1 | 11/2016 |
| WO | 2020/014325 A1 | 1/2020 |
| WO | 2020/014328 A1 | 1/2020 |

OTHER PUBLICATIONS

Jamalizadeh et al. (2009) "Quantum chemical studies on corrosion inhibition of some lactones on mild steel in acid media", Corrosion Science, 51(6):1428-1435.
Khamis et al. (1991) "Acid Corrosion Inhibition of Nickel by 2-(Triphenosphoranylidene) Succinic Anhydride", Corrosion, 47(9): 677-686.
Broggini et al. (1991) "Synthesis of 5-hydroxymethyl-1, 4-dioxan-2-one", Organic preparations and procedures international, 23(6):762-4.
Krevalis et al. (2006) "Investigation into the use of hydroxy-containing amides for oil flowable formulations", Journal of ASTM International, 3(1):293-303.
International Preliminary Report on Patentability for International Application No. PCT/US2019/041155, dated Jan. 21, 2021, 8 pages.
International Search Report and Written Opinion for International Application No. PCT/US2019/041152, dated Sep. 23, 2019, 6 pages.
International Preliminary Report on Patentability for International Application No. PCT/US2019/041152, dated Jan. 21, 2021, 9 pages.
International Search Report and Written Opinion for International Application No. PCT/US2019/041155, dated Oct. 25, 2019, 11 pages.
Detert et al. (1996) "Cationic amphiphiles with G-protein-stimulatory activity: Studies on the role of the basic domain in the activation process" Pharmazie, 2:67-72.
Goossen et al. (2010) "Silver triflate-catalysed synthesis of gamma-lactones from fatty acids", Green Chem., 12:197-200.
Miller et al. (2000) "5-HETE Congeners as Modulators of Cell Proliferation", Bioorganic & Medicinal Chemistry Letters, 10:1913-1916.
EIC Structure Search (Year:2020).

* cited by examiner

ALKYL LACTONE-DERIVED HYDROXYAMIDES AND ALKYL LACTONE-DERIVED HYDROXYESTERS FOR THE CONTROL OF NATURAL GAS HYDRATES

CROSS REFERENCE TO RELATED APPLICATIONS

This application is a continuation of U.S. patent application Ser. No. 16/507,873, filed Jul. 10, 2019, entitled "ALKYL LACTONE-DERIVED HYDROXYAMIDES AND ALKYL LACTONE-DERIVED HYDROXYESTERS FOR THE CONTROL OF NATURAL GAS HYDRATES," which claims the benefit of U.S. Provisional Application No. 62/697,153, entitled "ALKYL LACTONE-DERIVED HYDROXYAMIDES AND ALKYL LACTONE-DERIVED HYDROXYESTERS FOR THE CONTROL OF NATURAL GAS HYDRATES", filed Jul. 12, 2018, the contents of all of which are hereby incorporated in their enteritis by reference.

FIELD OF THE INVENTION

The application is directed at inhibiting or preventing the formation of natural gas hydrate agglomerates.

BACKGROUND

"Natural gas hydrates" is a term referring to ice-like solids that are formed from gas molecules and water dissolved within liquid petroleum products (liquid hydrocarbons) when the temperature of the liquid is lowered and/or pressure upon the liquid is increased. Under these conditions, water molecules can form cage-like structures around gas molecules such as carbon dioxide, hydrogen sulfide, methane, ethane, propane, butane and iso-butane, creating crystalline clathrate structures, also termed a "clathrate gas hydrates." The specific architecture of a cage structure can be one of several types (called type 1, type 2, type H), depending on the identity of the guest molecule(s).

Once formed, these crystalline cage structures tend to precipitate and settle out from the liquid, accumulating into large solid masses. Such masses that form in petroleum liquids such as oil obtained from a subterranean reservoir can travel in transporting pipelines, and potentially block or damage the pipelines, related equipment, or both. The damage resulting from a blockage can be costly because equipment and pipelines need to be repaired, and oil production and the safety of field workers can be adversely affected.

Petroleum liquid recovery and production commonly operate under high pumping speed and high pressure within processing and transportation pipelines, conditions particularly favorable for natural gas hydrate formation. Additionally, weather conditions in some field locations can cause a substantial drop in temperature during one or more production, transportation, and storage operations carried out during and after recovery of liquids obtained from subterranean reservoirs.

The industry uses a number of methods to prevent or reduce natural gas hydrate formation and its accompanying adverse effects. For example, natural gas hydrate inhibitors include thermodynamic gas hydrate inhibitors (THI), anti-agglomerant gas hydrate inhibitors (AAs), and kinetic gas hydrate inhibitors (KHIs). The amount of chemical needed to prevent blockages varies widely depending upon the inhibitor type employed. THIs are substances that can reduce the temperature at which the gas hydrates form at a given pressure and water content, and are typically dosed at 50% based on water content and as high as 100% of the volume of water. Therefore, there is a substantial cost associated with the transportation and storage of large quantities of these inhibitors. A more cost-effective alternative is the use of low dosage gas hydrate inhibitors (LDHIs), as they generally require a dose of less than about 2 volume percent to inhibit the nucleation or growth of gas hydrates. The two general types of LDHIs, KHIs and anti-agglomerants, typically are used at much lower concentrations.

KHIs work by delaying the growth of gas hydrate crystals. They also function as anti-nucleators. In contrast, AAs allow natural gas hydrates to form but prevent them from agglomerating and subsequently accumulating into larger masses capable of causing plugs. AAs function to keep natural gas hydrate crystals and agglomerates dispersed as a slurry within the liquid hydrocarbon.

While many inhibitors and dispersants have been developed for ameliorating the effects of natural gas hydrates within liquid petroleum products, there continues to be a need for new and effective compositions and methods of preventing or reducing natural gas hydrate agglomerate formation. There is also an ongoing need for these compounds to be less toxic with respect to the environment.

SUMMARY

Described herein are compositions and methods for inhibiting the formation of natural gas hydrate agglomerates in a fluid comprising water, gaseous molecules, and a liquid hydrocarbon.

In one aspect of the invention is a composition comprising at least one alkyl lactone-derived hydroxyamide or alkyl lactone-derived hydroxyester to inhibit formation of natural gas hydrate agglomerates, the at least one alkyl lactone-derived hydroxyamide formed by a reaction between an alkyl lactone with an amine, and the alkyl lactone-derived hydroxyester formed by a reaction between an alkyl lactone with an alcohol.

In another aspect of the invention is a composition comprising:
  a fluid; and
  the alkyl lactone-derived hydroxyamide or alkyl lactone-derived hydroxyester.

In yet another aspect of the invention is a method of inhibiting formation of agglomerates of natural gas hydrates comprising:
  introducing into a fluid a composition comprising at least one alkyl lactone-derived hydroxyamide or alkyl lactone-derived hydroxyester to inhibit formation of agglomerates of natural gas hydrates, the at least one alkyl lactone-derived hydroxyamide formed by a reaction between an alkyl lactone with an amine, and the alkyl lactone-derived hydroxyester formed by a reaction between an alkyl lactone with an alcohol.

The above-described compositions and methods are suitable for use in aquatic environments as they have lower toxicities.

DETAILED DESCRIPTION

Figure 1:
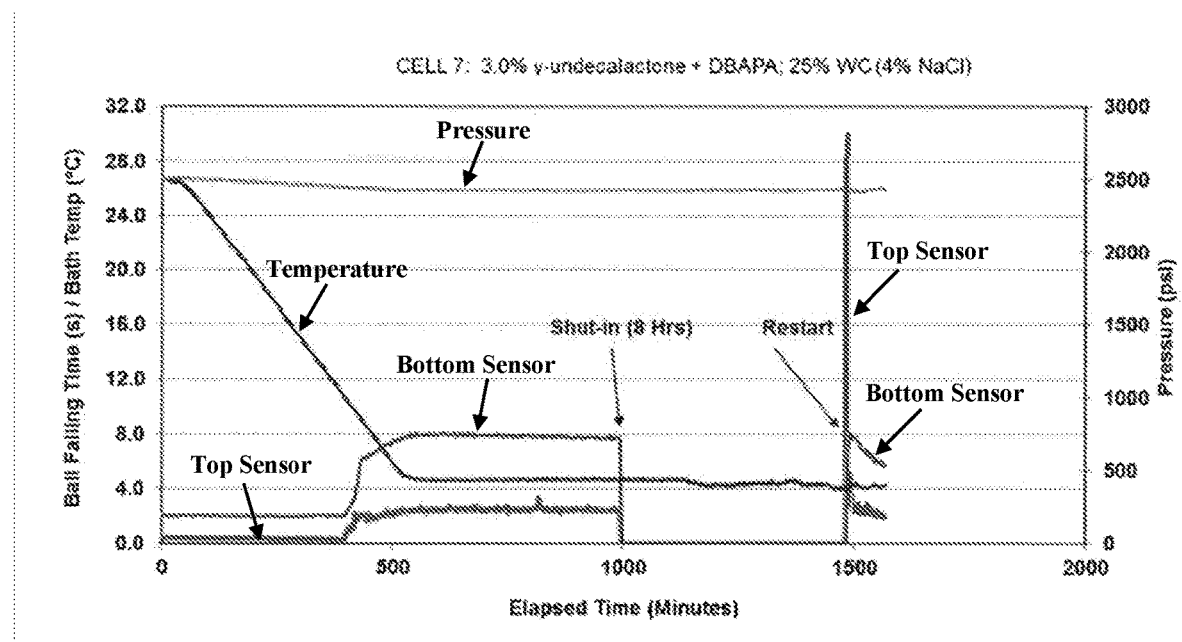
FIG. 1 is a graphical representation of cell pressure as a function of run time for a formulation of an embodiment of the invention.

Although the present disclosure provides references to various embodiments, persons skilled in the art will recognize that changes may be made in form and detail without departing from the spirit and scope of the invention. Various embodiments will be described in detail with reference to the figures. Reference to various embodiments does not limit the scope of the claims attached hereto. Additionally, any examples set forth in this specification are not intended to be limiting and merely set forth some of the many possible embodiments for the appended claims.

Unless otherwise defined, all technical and scientific terms used herein have the same meaning as commonly understood by one of ordinary skill in the art. In case of conflict, the present document, including definitions, will control. Methods and materials are described below, although methods and materials similar or equivalent to those described herein can be used in practice or testing of the present invention. All publications, patent applications, patents and other references mentioned herein are incorporated by reference in their entirety.

As used herein, the term "alkyl" refers to a monovalent group derived by the removal of a single hydrogen atom from a straight or branched chain or cyclic saturated or unsaturated hydrocarbon containing from one to sixty carbon atoms.

As used herein, the term "anti-agglomerant" or "AA" refers to a compound that inhibits formation of agglomerates of natural gas hydrates. The term will be understood to refer to the AA itself or in a composition which may include other AAs or compounds or solvents, as determined by context.

As used herein, the term "fluid" means liquid, gas molecules, or both in an oil or natural gas well production operation.

As used herein, the term "inhibits," "inhibiting," or grammatical equivalents thereof refers to preventing, retarding, mitigating, reducing, controlling and/or delaying formation of gas hydrates and/or agglomerates of gas hydrates, and/or equipment/pipeline plugs formed from gas hydrate agglomerates.

As used herein, the terms "natural gas hydrates" or "gas hydrates" refers to a gaseous mixture in a water clathrate.

As used herein, the terms "comprise(s)," "include(s)," "having," "has," "can," "contain(s)," and variants thereof are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

As used herein, the term "optional" or "optionally" means that the subsequently described event or circumstance may but need not occur, and that the description includes instances where the event or circumstance occurs and instances in which it does not.

As used herein, the term "about" modifying, for example, the quantity of an ingredient in a composition, concentration, volume, process temperature, process time, yield, flow rate, pressure, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities. Further, where "about" is employed to describe a range of values, for example "about 1 to 5" the recitation means "1 to 5" and "about 1 to about 5" and "1 to about 5" and "about 1 to 5" unless specifically limited by context.

As used herein, the term "substantially" means "consisting essentially of" and includes "consisting of" "consisting essentially of" is construed as in U.S. patent law, and "consisting of" is construed as in U.S. patent law. For example, a solution that is "substantially free" of a specified compound or material may be free of that compound or material, or may have a minor amount of that compound or material present, such as through unintended contamination, side reactions, or incomplete purification. A "minor amount" may be a trace, an unmeasurable amount, an amount that does not interfere with a value or property, or some other amount as provided in context. A composition that has "substantially only" a provided list of components may consist of only those components, or have a trace amount of some other component present, or have one or more additional components that do not materially affect the properties of the composition. Additionally, "substantially" modifying, for example, the type or quantity of an ingredient in a composition, a property, a measurable quantity, a method, a value, or a range, employed in describing the embodiments of the disclosure, refers to a variation that does not affect the overall recited composition, property, quantity, method, value, or range thereof in a manner that negates an intended composition, property, quantity, method, value, or range. Where modified by the term "substantially" the claims appended hereto include equivalents according to this definition.

As used herein, any recited ranges of values contemplate all values within the range and are to be construed as support for claims reciting any sub-ranges having endpoints which are real number values within the recited range. By way of example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

Described are compositions and methods to inhibit formation of agglomerates of natural gas hydrates, and/or plugs formed from natural gas hydrate agglomerates within liquid hydrocarbon recovery, processing, transportation, and storage operations. The compositions may be applied to one or more liquid hydrocarbon products to inhibit plugging of annular spaces, such as pipes, transfer lines, valves, and the like, including equipment downhole where the conditions are conducive for the formation of gas hydrates.

In embodiments, the compounds used in the compositions and methods for inhibiting gas hydrate agglomerates are alkyl lactone-derived hydroxyamides and alkyl lactone derived-hydroxyesters. The compounds are formed by the reaction of alkyl lactones and amines, or alkyl lactones and alcohols. Such alkyl lactone-derived compounds have the general formula shown below as formula I, wherein X=nitrogen or oxygen;
wherein $R^1$=any fatty tail derived from 1-30 carbon saturated or unsaturated alkyl group or a ring structure including cyclohexyl, cyclopentyl, phenyl, benzyl, or variants thereof;
wherein $R^2$=is H or any 1-10 carbon saturated or unsaturated alkyl group or a ring structure which would link to $R^3$; and
wherein $R^3$=H or any 1-10 carbon saturated or unsaturated alkyl group or a ring structure which would link to $R^2$, e.g. pyrrolidine or azepane, and the like.

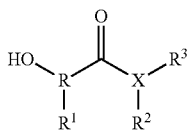

Formula I

In embodiments, the alkyl lactone-derived hydroxyamide is shown below as formula II, III and IV, with the various groups as previously described.

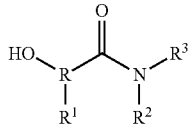

Formula II

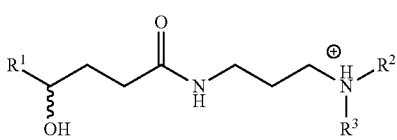

Formula III

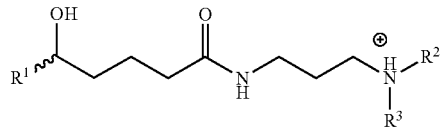

Formula IV wherein, $R^1$=any fatty tail including C1-C30 saturated or unsaturated alkyl group or a ring structure including cyclohexyl, cyclopentyl, phenyl, benzyl, or variants thereof;
wherein $R^2$=H or any C1-C10 saturated or unsaturated alkyl group or being a ring structure which would link to $R^3$; and
wherein $R^3$=H or any C1-C10 saturated or unsaturated alkyl group or being a ring structure which would link to $R^2$, e.g. pyrrolidine or azepane, and the like.

In embodiments, $R^2$ and $R^3$ are individually selected from isopropyl, butyl, pentyl, isobutyl or isopentyl groups. In embodiments, $R^2$ and $R^3$ individually may include one or more aminopropylamine chains such as dibutylaminopropylamine (DBAPA) or a DBAPA with additional aminopropylamine referred herein as an extended DBAPA. In embodiments, $R^2$=$R^3$. In embodiments, $R^2$ and $R^3$ are individually derived from the following amines:

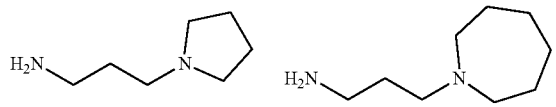

Aminopropyl pyrrolidine    Aminopropyl azepane and

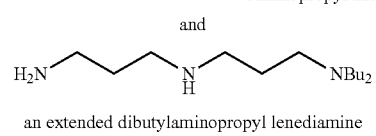

an extended dibutylaminopropyl lenediamine

In embodiments, the alkyl lactone-derived hydroxyamides include one or more of the following structures or a combination thereof:

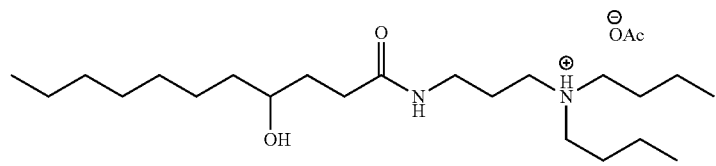

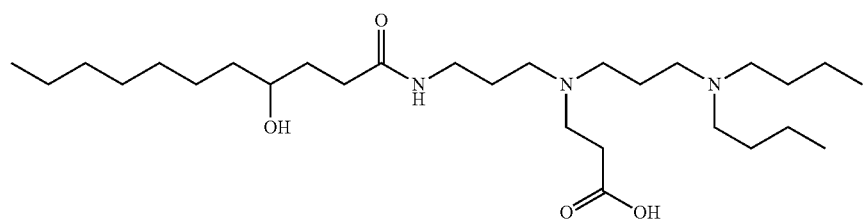

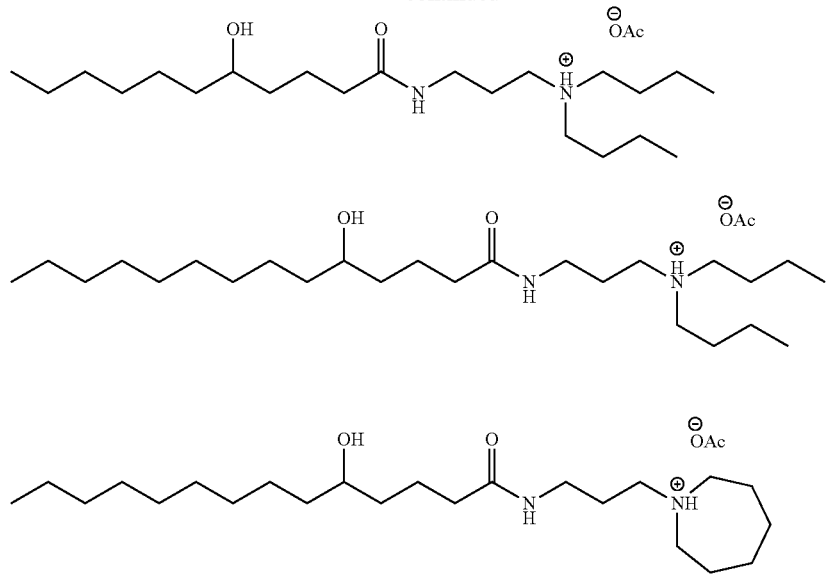

Any suitable method may be used to synthesize the alkyl lactone-derived hydroxyamides. The synthesis of the alkyl lactone-derived hydroxyamides is not limited by the described processes.

In embodiments, the alkyl lactone-derived hydroxyamides are obtained by reacting alkyl lactones with amines as shown below, wherein $R^1$ is an alkyl moiety and $R^2$ and $R^3$ are selected from H or an alkyl group, with the proviso that only one of $R^2$ and $R^3$ may be H.

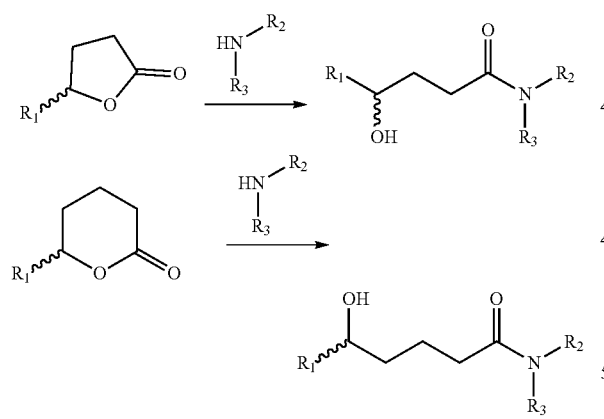

In embodiments, the alkyl lactone-derived hydroxyamide is formed by reacting an alkyl lactone and an aminopropyl amine followed by acidification as shown below. wherein $R^1$=any fatty tail is derived from C1-C30 saturated or unsaturated alkyl group or a ring structure including cyclohexyl, cyclopentyl, phenyl, benzyl, or variants thereof; and wherein $R^2$ and $R^3$ are an H or an alkyl group with the proviso that only one of $R^2$ and $R^3$ may be H.

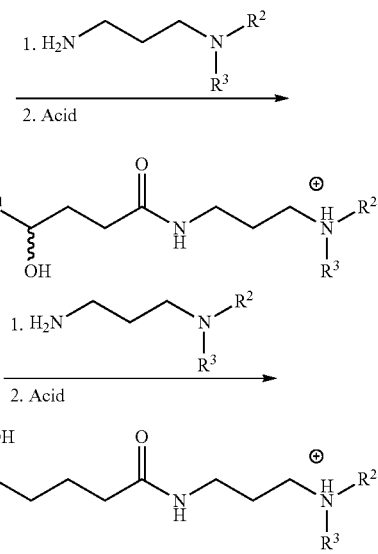

In embodiments, the alkyl lactone-derived hydroxyamide is formed by reacting the alkyl lactone, which is a γ-undecalactone and an amine, which is dibutylaminopropylamine. The resultant alkyl lactone-derived hydroxyamide is followed by acidification with acetic acid:

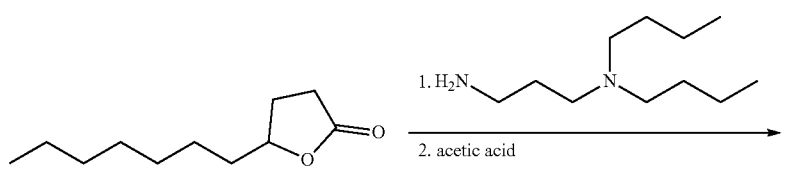

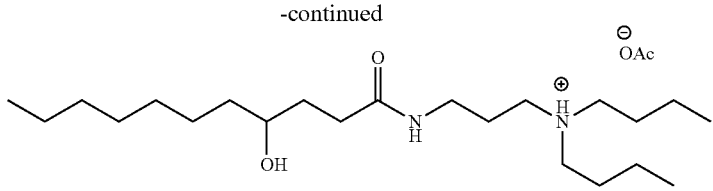

In embodiments, the alkyl lactone-derived hydroxyamide is the reaction product of γ-undecalactone with dibutylamine:

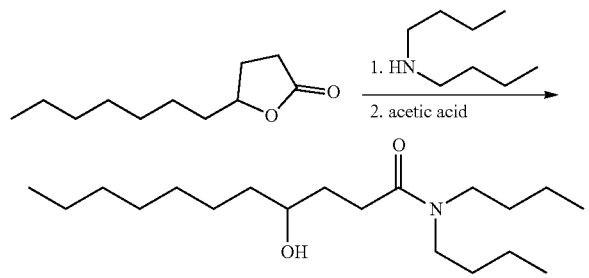

In embodiments the alkyl lactone-derived hydroxyamide is a reaction product of an alkyl lactone with dibutylamine, dibutylaminopropylamine, or a dibutylaminopropylamine with an additional aminopropylamine (extended DBAPA).

In other embodiments, the alkyl lactone-derived hydroxyamides are reaction products as shown below:

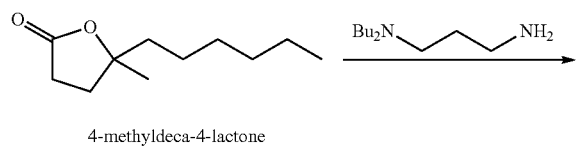

4-methyldeca-4-lactone

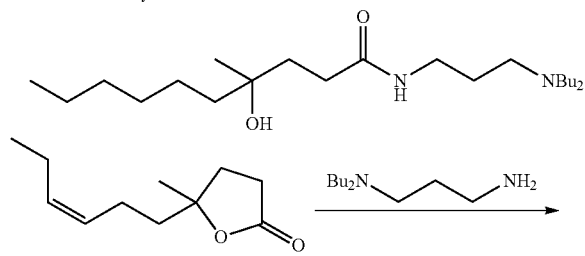

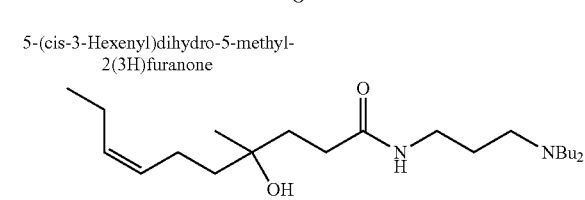

5-(cis-3-Hexenyl)dihydro-5-methyl-2(3H)furanone

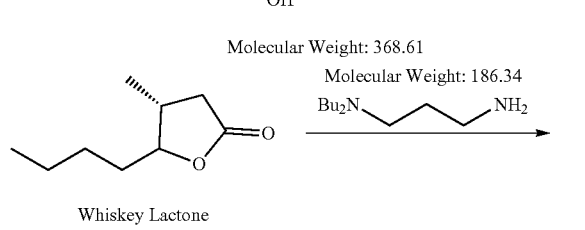

Molecular Weight: 368.61

Molecular Weight: 186.34

Whiskey Lactone

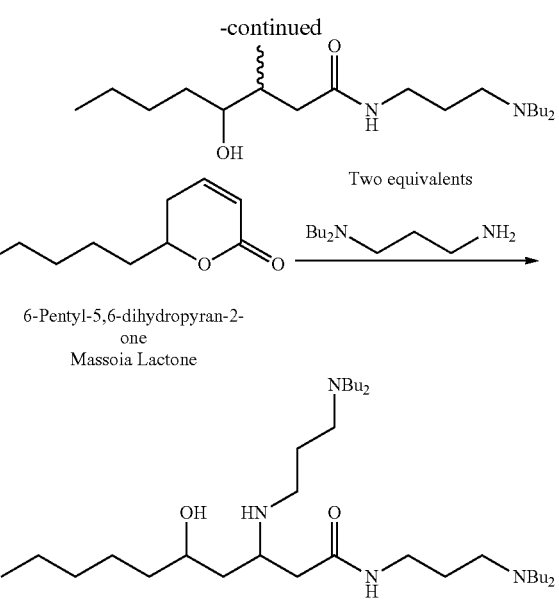

Two equivalents

6-Pentyl-5,6-dihydropyran-2-one
Massoia Lactone

Molecular Weight: 540.92

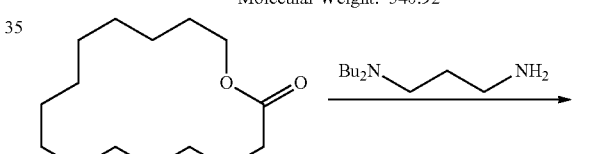

OMEGA-PENTADECALACTONE
Reference: Notebook 7630-40

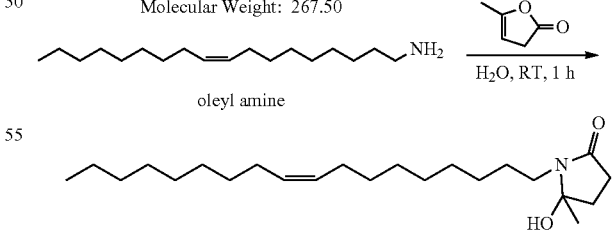

Molecular Weight: 267.50 oleyl amine

In some embodiments, the compositions and methods useful for inhibiting gas hydrates and agglomerates of gas hydrates is an alkyl lactone-derived hydroxyester. In embodiments, the alkyl lactone-derived hydroxyester is a reaction product of an alkyl lactone with an alcohol, and as shown below, wherein $R^1$ is an alkyl moiety (as described above), and $R^2$ is an alkyl group.

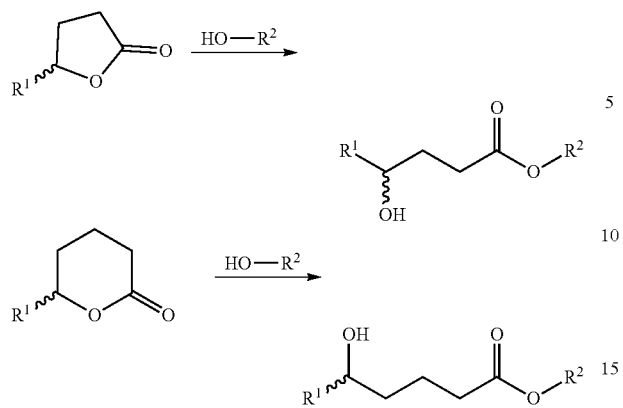

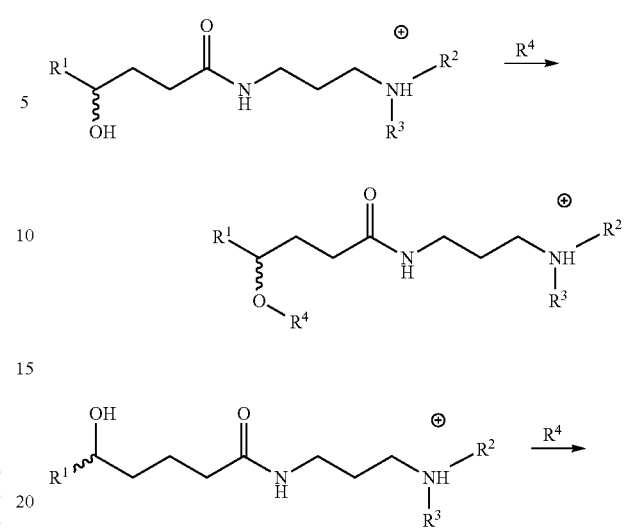

In embodiments, the alkyl lactone-derived hydroxyester is the reaction product of γ-undecalactone reacted with dibutylaminoethanol, followed by acidification to form the ammonium salt of the tertiary amino moiety:

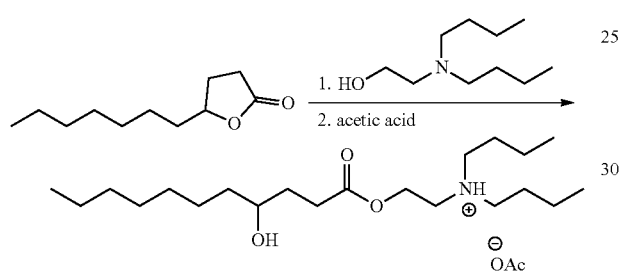

In embodiments, the hydroxyl of the alkyl lactone-derived hydroxyester or alkyl lactone-derived hydroxyamide can be further modified. In embodiments, the resultant hydroxyl is modified by displacing the hydrogen of the hydroxyl to form an O-bonded moiety. Suitable O-bonded moieties include ether, carboxylic acid, silyl ether, and the like. In embodiments, suitable O-bonded moieties are shown below, wherein $R^1$ is as described previously, and $R^4$ is alkyl, silyl, carboxyl, and the like.

In embodiments, the O-bonded moiety is the reaction product of the alkyl lactone-derived hydroxyamide or alkyl lactone-derived hydroxyester with maleic anhydride or other anhydride moiety. For example, the alkyl lactone-derived hydroxyamide (which is a reaction between γ-undecalactone with dibutylaminopropylamine) is further reacted with maleic anhydride as follows:

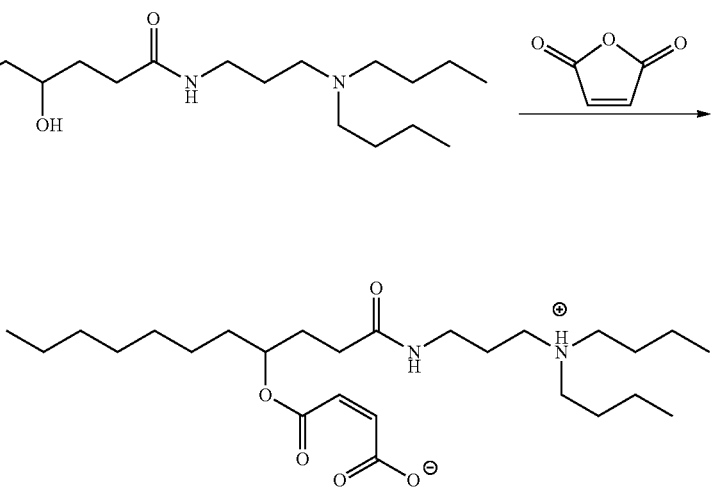

In embodiments, the ether is formed from the alkyl lactone-derived hydroxyamide by reacting with a bromide. In embodiments, the alkyl lactone-derived hydroxyamide is formed by reacting γ-undecalactone with DBAPA. The resultant alkyl lactone-derived hydroxyamide is further reacted with n-butyl bromide to yield a corresponding ether as follows:

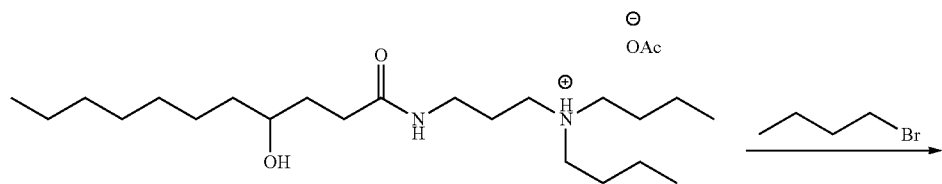

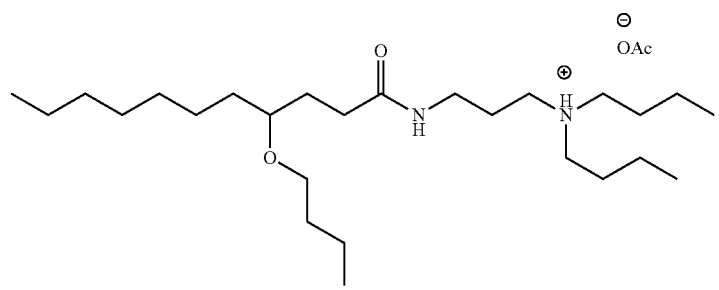

In still other embodiments, the resultant hydroxyl of the alkyl lactone-derived hydroxyamide is modified by oxidation to a ketone. For example, oxidation to a ketone is as shown below, wherein $R^1$ is as described above, and the newly formed ketone can be left as-is or further reacted with amines (Schiff base formation, reductive amination, and the like), or reacted via aldol reactions, Mannich reactions, and the like.

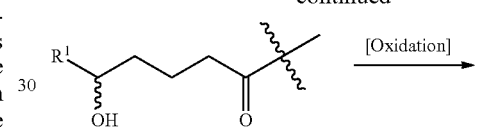

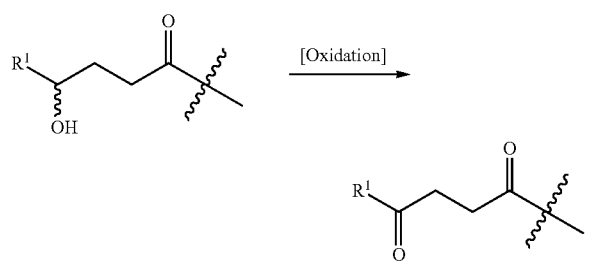

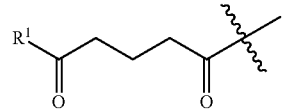

In embodiments, the oxidation can be with yridinium chlorochromate (PCC) to yield a ketone as shown below:

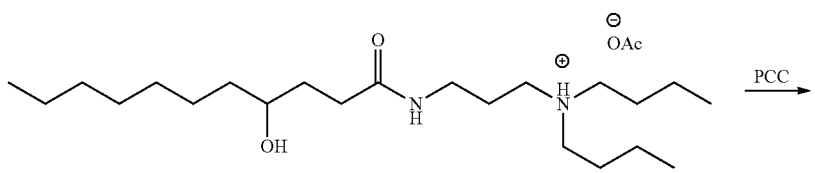

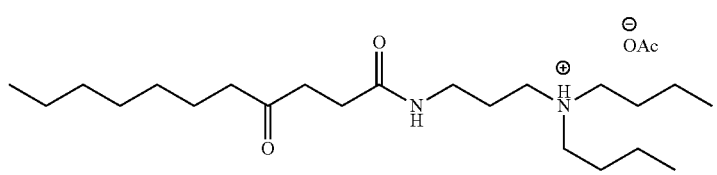

The resultant alkyl lactone-derived hydroxyamide and alkyl lactone-derived hydroxyester result from reactions with alkyl lactones. In embodiments, the alkyl lactones have at least two carbon atoms in the lactone ring. In embodiments, the lactones are from 2-30 or 5-20 carbon atoms. In embodiments, the alkyl lactones are gamma-alkyl lactones and delta-alkyl lactones. In embodiments, the alkyl lactones are beta, epsilon, or larger variants such as omega-alkyl lactones (for example w-pentadecalactone). In embodiments, the variability in the alkyl moiety are at the gamma or delta carbon, but can occur along the alpha, beta, gamma, delta, or epsilon position along the lactone ring, in multiple locations and chiralities.

In embodiments, the alkyl chain is a straight chain alkyl having 1-30 carbon straight or branched chain alkyl. In other embodiments, the alkyl chain is a branching, unsaturation or additional functionality. In embodiments, unsubstituted alkyl groups include methyl, ethyl, n-propyl, i-propyl, n-butyl, i-butyl, s-butyl, t-butyl, n-pentyl, i-pentyl, s-pentyl, t-pentyl, hexyl, heptyl, octyl, nonyl, decyl, lauryl, and the like.

In embodiments, the alkyl lactones are either synthetic or natural. In embodiments, the synthetic lactones can be produced from fatty acids plus acrylic acid and peroxide.

In embodiments, the lactones are naturally produced, where they are commonly used as food additives or flavor/fragrance molecules. In embodiments, natural lactones include cis-3-methyl-4-octanolide (whisky lactone), massoia lactone (6-pentyl-5,6-dihydropyran-2-one), 5-(cis-3-hexenyl)dihydro-5-methyl-2(3H)furanone, 4-methyldeca-4-lactone, angelica lactone and the like.

In embodiments, commercially available lactones, for example from Sigma Aldrich include 4-methyldeca-4-lactone, whisky lactone, omega-pentadecalactone, and 6-pentyl-5,6-dihydropyran-2-massoia lactone.

Any suitable amine may be used to react with the alkyl lactone to result in the described alkyl lactone-derived hydroxyamide. The amine may be characterized by the presence of at least one primary, secondary or tertiary amino group.

In embodiments, the amine is a monoamine, diamine or polyamine. Examples of monoamines include ethylamine, dimethylamine, diethylamine, n-butylamine, dibutylamine, allylamine, isobutylamine, cocoamine, stearylamine, laurylamine, methyllaurylamine, oleylamine, N-methyl-octylamine, dodecyl-amine, diethanolamine, morpholine, and octadecyl amine.

In other embodiments, the amines are diamines, which can include aliphatic diamines, branched aliphatic diamines, cyclic diamines.

In embodiments, the polyamines have the formula [R⁵—NH—R⁶], wherein $R^5$ and $R^6$ are a H or an alkyl group.

In embodiments, the amine is a dibutylaminopropylenediamine:

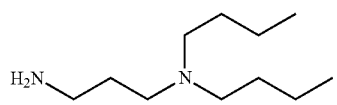

In other embodiments, the amine is a dibutylaminopropylenediamine with an additional aminopropylamine:

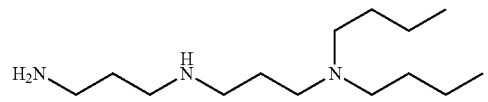 [SMILES: CCCCN(CCCC)CCCNCCCN]

In embodiments, polyalkylene polyamines of about 2 to 60, 2 to 40, 3 to 20 total carbon atoms and about 1 to 12, 3 to 12, 5 to 9 nitrogen atoms in the molecule.

In embodiments, amines are hydrocarbyl amines or hydrocarbyl amines including other groups, e.g., hydroxy groups, alkoxy groups, amide groups, nitriles, imidazoline groups, and the like. Hydroxy amines with 1 to 6 hydroxy groups or 1 to 3 hydroxy groups are useful.

In embodiments, amines are aliphatic saturated amines, including those of the general formulas:

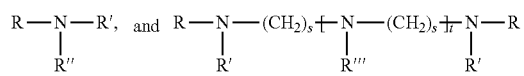

wherein R, R', R" and R'" are independently selected from a group of hydrogen; 1 to 25 carbon straight or branched chain alkyl radicals; 1 to 12 carbon alkoxy, 2 to 6 carbon alkylene radicals; 2 to 12 carbon hydroxy amino alkylene radicals; and 1 to 12 carbon alkylamino, 2 to 6 carbon alkylene radicals; and wherein R'" can additionally comprise a moiety of the formula:

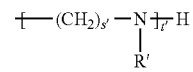

wherein R' is as defined above, and wherein s and s' can be the same or a different number of from 2 to 6, 2 to 4; and t and t' can be the same or different and are numbers of from 0 to 10, 2 to 7, or about 3 to 7, with the proviso that the sum of t and t' is not greater than 15.

In embodiments, exemplary amine compounds include: 1,2-diaminoethane; 1,3-diaminopropane; 1,4-diaminobutane; 1,6-diaminohexane: polyethylene amines such as diethylene triamine; triethylene tetramine; tetraethylene pentamine; polypropylene amines such as 1,2-propylene diamine; di-(1,2-propylene)triamine; di-(1,3-propylene) triamine; N,N-dimethyl-1,3-diaminopropane; N,N-di-(2-aminoethyl) ethylene diamine; N,N-di(2-hydroxyethyl)-1,3-propylene diamine; 3-dodecyloxypropylamine; N-dodecyl-1,3-propane diamine; tris hydroxymethylaminomethane (THAM); diisopropanol amine; diethanol amine; triethanol amine; mono-, di-, and tri-tallow amines; amino morpholines such as N-(3-aminopropyl)morpholine; and mixtures thereof.

Any suitable alcohol may be used to react the alkyl lactone to result in the disclosed alkyl lactone-derived hydroxyester. In embodiments, alcohols having the formula: OH—R⁷ are used, wherein R⁷ is an alkyl, aryl or alkaryl hydrocarbyl group having from one to twenty carbons, and wherein R⁷ may be C1-C20 unsubstituted or substituted alkyl, C2-C20 unsubstituted or substituted alkenyl, C2-C20 unsubstituted or substituted alkynyl, C3-C20 unsubstituted or substituted cycloalkyl, C3-C20 unsubstituted or substituted cycloalkyl containing at least one heteroatom, C6-C20 unsubstituted or substituted aryl, C6-C20 unsubstituted or substituted aryl containing at least one heteroatom, C7-C20 unsubstituted or substituted alkaryl, or C7-C20 unsubstituted or substituted alkaryl containing at least one heteroatom.

In embodiments, the alcohols are methanol, ethanol, propanol, i-propanol, n-butanol, i-butanol, t-butanol, n-octanol, hexanol, cyclohexanol and benzyl alcohol or combinations thereof. In embodiments, the alcohol is an amino alcohol. Amino alcohols include the 2,2-disubstituted-2-amino-1-alkanols having from two to three hydroxy groups and containing a total of 4 to 8 carbon atoms. This amino alcohol can be represented by the formula:

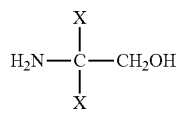

wherein X is an alkyl or hydroxyalkyl group with the alkyl groups having from 1 to 3 carbon atoms wherein at least one, and preferably both, of the X substituents is a hydroxyalkyl group of the structure —$(CH_2)_n$ OH, n being 1 to 3.

In embodiments, the alcohols are amino alcohols. Examples of amino alcohols include 2-amino-2-methyl-1,3 propanediol, 2-amino-2-ethyl-1,3-propanediol, and 2-amino-2-(hydroxymethyl)1,3-propanediol, (THAM or tris (hydroxymethyl) amino methane). In other embodiments, the alcohol is a dibutylaminoethanol, diethylaminoethanol, dipropylaminoethanol, diisopropyl, diisobutyl, diisopentyl, dipentyl and diisohexyl/dihexyl.

In embodiments, the acidification step is of a secondary or tertiary amine. In embodiments, the acidification is generally achieved through the addition of an organic acid. Exemplary organic acids include acetic acid or acrylic acid. In other embodiments, the acrylic acid reactions with any residual primary or secondary amines (reversibly with tertiary amines) to yield a carboxybetaine structure. Other organic acids may be used for this acidification, including pivalic acid, malic acid, maleic acid, succinic acid, and any C1-C12+ carboxylic acids. Inorganic acids can also be used, such as common mineral acids (hydrochloric acid, phosphoric acid, nitric acid, carbonic acid) or related, as well as Lewis acids (tetrafluoroborate, aluminum trichloride, or the like).

The compositions and methods described herein are used to inhibit formation of agglomerates of gas hydrates, and plugging during liquid hydrocarbon production and transportation. In embodiments, compositions comprise, consist of or consist essentially of at least one of the described alkyl lactone-derived hydroxyamides or alkyl lactone-derived hydroxyesters. In embodiments, the composition can further comprise one or more thermodynamic gas hydrate inhibitors, one or more kinetic gas hydrate inhibitors, one or more other AAs, or any combination thereof. In some embodiments, the composition can include other additives such as one or more asphaltene inhibitors, paraffin inhibitors, corrosion inhibitors, scale inhibitors, demulsifies, water clarifiers, dispersants, emulsion breakers, or any combination thereof. In embodiments, compositions include the disclosed alkyl lactone-derived hydroxyamides or alkyl lactone-derived hydroxyesters with one or more corrosion inhibitors as disclosed in U.S. Provisional Application Ser. No. 62/697, 165).

The composition comprising the alkyl lactone-derived hydroxyamides or alkyl lactone-derived hydroxyesters is prepared or formulated in one or more solvents, depending upon the application and requirements. In embodiments, suitable solvents for formulation with the alkyl lactone-derived hydroxyamide or alkyl lactone-derived hydroxyester composition include water, brine, seawater, alcohols such as methanol, ethanol, isopropanol, n-propanol, n-butanol, isobutanol, sec-butanol, t-butanol or higher alcohols such as benzyl alcohol); ketones such as acetone, or methyl ethyl ketone (2-butanone); acetonitrile; esters such as ethyl acetate, propyl acetate and butyl acetate; ethers such as diethyl ether or higher, e.g. methyl t-butyl ether, glyme, diglyme, ethylene glycol monobutyl ether, ethylene diglycol ethyl ether, 1,4 dioxane and related glycols; aromatics such as toluene, xylene(s), diethylbenzene, naphthalene and related aromatics or refinery cuts (heavy aromatic naphtha, heavy aromatic distillates, and related); aliphatics such as pentane, hexane, heptane, octane, or refined gasoline; or several "green" solvents such as 2-methyltetrahydrofuran, furfural alcohol, and cyclopentylmethylether.

In embodiments, other solvents suitable for formulation with the alkyl lactone-derived hydroxyamide or alkyl lactone-derived hydroxyester include aliphatics, such as pentane, hexane, cyclohexane, methylcyclohexane, heptane, decane, dodecane, diesel, and the like, and aromatics, such as toluene, xylene, heavy aromatic naphtha, fatty acid derivatives (acids, esters, amides), and the like.

In embodiments, the alkyl lactone-derived hydroxyamide or alkyl lactone-derived hydroxyester is formulated in a composition with an amount from about 1-80 w/v %. In embodiments, the alkyl lactone-derived hydroxyamide or alkyl lactone-derived hydroxyester is added in an amount from about 1-10 w/v %, 10-20 w/v %, 20-60 w/v %, 45-60 w/v %, 60-80 w/v %, or 1-60 w/v %.

In embodiments, the composition comprising the alkyl lactone-derived hydroxyamide or alkyl lactone-derived hydroxyester is used in a method of inhibiting the formation of natural gas hydrate agglomerants. The method comprises adding to a fluid an amount of a composition comprising one or more alkyl lactone-derived hydroxyamides or alkyl lactone-derived hydroxyesters. In embodiments, the fluid comprises water, gas molecules, and liquid hydrocarbon.

An exemplary application point for the petroleum liquid production operations is near the surface controlled sub-sea safety valve. In embodiments, application or introduction of the hydroxyamides or hydroxyesters is into a downhole. This ensures that during a shut-in, the composition is able to disperse throughout the area where natural gas hydrates will occur. Application of the alkyl lactone-derived hydroxyamides or alkyl lactone-derived hydroxyesters can also occur at other areas in the flowline, taking into account the density of the injected liquid. If the injection point is well above the gas hydrate formation depth, then the alkyl lactone-derived hydroxyamide or alkyl lactone-derived hydroxyester may be formulated with a solvent having a density high enough that the alkyl lactone-derived hydroxyamide or alkyl lactone-derived hydroxyester will sink in the flowline to collect at the water/oil interface. In embodiments, application is also used in pipelines or anywhere in the system where the potential for agglomerates of gas hydrate formation exists.

In embodiments, various dosage amounts of the alkyl lactone-derived hydroxyamide or alkyl lactone-derived hydroxyester or compositions containing them are introduced to the fluid to inhibit the formation of gas hydrate agglomerants. One of ordinary skill in the art is able to calculate the amount of a composition comprising the alkyl lactone-derived hydroxyamide or alkyl lactone-derived hydroxyester for a given situation without undue experimentation. Factors that would be considered important in such calculations include, for example, content of fluid, percentage water cut, API gravity of hydrocarbon. In embodiments, the alkyl lactone-derived hydroxyamide or alkyl lactone-derived hydroxyester alone or in a composition is introduced into a fluid to be treated from about 1000 ppm to about 50,000 ppm, from about 2000 ppm to about 15,000 ppm, or 3000 ppm to 20,000 ppm.

The composition and methods are useful for inhibiting gas hydrate agglomerate formation for many hydrocarbons and hydrocarbon mixtures. The compositions are particularly useful for lighter or low-boiling, 1-5 carbon containing hydrocarbon gases or gas mixtures at ambient conditions. In embodiments, the gases are methane, ethane, propane, n-butane, isobutane, isopentane, and mixtures thereof. In other embodiments, natural gas mixtures are present in many gas and/or oil formations and natural gas liquids. The hydrocarbons may also comprise other compounds including, but not limited to, carbon dioxide, hydrogen sulfide, and other compounds commonly found in gas/oil formations or processing plants, either naturally occurring and/or used in recovering/processing hydrocarbons from the formation, and mixtures thereof.

In embodiments, the compositions and methods are useful for inhibiting gas hydrate formation in a variety of black oils, heavy black oils to condensates, from API 20-50. In embodiments, the compositions and methods are useful for inhibiting gas hydrate formation in paraffinic or asphaltenic oils. In such embodiments, paraffin or asphaltene inhibitors are used in conjunction with the alkyl lactone-derived hydroxyamide or alkyl lactone-derived hydroxyester.

In embodiments, the composition comprising the alkyl lactone-derived hydroxyamide or alkyl lactone-derived hydroxyester is applied to fluids that containing various levels of oil, brine or both having various levels of salinity. In one embodiment, the fluid has a salinity of about 0.1% to about 25% or about 10% to about 25% weight/weight (w/w).

In some embodiments, the composition comprising the alkyl lactone-derived hydroxyamide or alkyl lactone-derived hydroxyester is applied to a fluid that contains various levels of water cut. One of ordinary skill in the art understands that "water cut" refers to the percent of water in a composition containing an oil and water mixture. In one embodiment, the water cut is from about 1% to about 80% w/w with respect to the hydrocarbon phase. In other embodiments, the water cut is from about 1% to about 30% w/w, from about 5% to about 40% w/w, from about 10% to about 60% w/w, from about 15% to about 80% w/w with respect to the hydrocarbon phase.

The methods can be used at any pressure that results in hydrocarbon gas hydrates. When the hydrocarbons in the mixture are lower boiling hydrocarbons or hydrocarbon gases at ambient conditions, the pressure is usually at or greater than atmospheric pressure (e.g., about 101 kPa), greater than about 1 MPa, or greater than about 5 MPa. The pressure in certain formation or processing units or plants could be much higher, such as greater than about 20 MPa. There is no specific high-pressure limit.

The composition comprising the alkyl lactone-derived hydroxyamide or alkyl lactone-derived hydroxyester may be introduced by any method suitable for ensuring dispersal of the alkyl lactone-derived hydroxyamide or alkyl lactone-derived hydroxyester through the liquid being treated. In some embodiments, the alkyl lactone-derived hydroxyamide or alkyl lactone-derived hydroxyester may be injected prior to substantial formation of gas hydrates.

In some embodiments, the alkyl lactone-derived hydroxyamide or alkyl lactone-derived hydroxyester is introduced into fluid contained in an oil and gas pipeline. In other embodiments, the alkyl lactone-derived hydroxyamide or alkyl lactone-derived hydroxyester is added to fluid contained in refineries, such as separation vessels, dehydration units, gas lines, and pipelines. In embodiments, the alkyl lactone-derived hydroxyamide or alkyl lactone-derived hydroxyester compositions are introduced into a fluid using various well-known methods and they may be introduced at numerous, different locations throughout a given system. In other embodiments, the composition comprising the one or more alkyl lactone-derived hydroxyamide or alkyl lactone-derived hydroxyester is injected using mechanical equipment such as chemical injection pumps, piping tees, injection fittings, and the like.

The alkyl lactone-derived hydroxyamide or alkyl lactone-derived hydroxyester are mixed or blended with mechanical mixing equipment or devices, stationary mixing setup or equipment, magnetic mixing or other suitable methods, to provide adequate contact and/or dispersion of the composition into the mixture. The introducing of the alkyl lactone-derived hydroxyamide or alkyl lactone-derived hydroxyester can be made in-line and/or offline. The various components of the composition may be mixed prior to and/or during introduction. One of skill will understand that the methods disclosed herein are not limited in any way by the timing or location of the introducing.

In embodiments, the alkyl lactone-derived hydroxyamide or alkyl lactone-derived hydroxyesters have increased biodegradation, lower toxicity, lower bioaccumulation or combination thereof. In embodiments, the alkyl lactone-derived hydroxyamide or alkyl lactone-derived hydroxyesters have a biodegradation of greater than 10%, greater than 20%, greater than 30%, greater than 40%, greater than 50% or greater than 60% when measured in a 28 day degradation test.

In embodiments, the alkyl lactone-derived hydroxyamide or alkyl lactone-derived hydroxyesters have reduced toxicity as measured in a 48 hour acute toxicity test with Daphnia magna of greater than or equal to 10 mg/ml. In embodiments, the alkyl lactone-derived hydroxyamide or alkyl lactone-derived hydroxyester has a 48-hour $EC_{50}$ value with Daphnia magna from about 10-100 mg/ml, 10-20 mg/ml, 15-25 mg/ml, 20-35 mg/ml, 30-40 mg/ml, 35-50 mg/ml, 40-60 mg/ml, 50-80 mg/ml, 60-90 mg/ml, or 70-100 mg/ml.

Some additional non-limiting embodiments are provided below to further exemplify the present disclosure:

Embodiment 1: A composition comprising at least one alkyl lactone-derived hydroxyamide or alkyl lactone-derived hydroxyester to inhibit formation of natural gas hydrate agglomerates, the at least one alkyl lactone-derived hydroxyamide formed by a reaction between an alkyl lactone with an amine, and the alkyl lactone-derived hydroxyester formed by a reaction between an alkyl lactone with an alcohol.

Embodiment 2: The composition of embodiment 1, wherein the alkyl lactone comprises 2 to 30 carbon atom-containing lactone.

Embodiment 3: The composition as in one of embodiments 1-2, wherein the alkyl lactone comprises 1-30 carbon atom-containing alkyl substituents.

Embodiment 4: The composition as in one of embodiments 1-3, wherein the alkyl lactone is a decalactone, or tetradecalactone.

Embodiment 5: The composition as in one of embodiments 1-4, wherein the amine comprises primary, secondary or tertiary amine.

Embodiment 6: The composition as in one of embodiments 1-5, wherein the amine is a dibutylaminopropylenediamine, a dibutylaminopropylenediamine with an additional aminopropylamino moiety, or combination thereof.

Embodiment 7: The composition as in one of embodiments 1-6, wherein the alkyl lactone-derived hydroxyamide comprises:

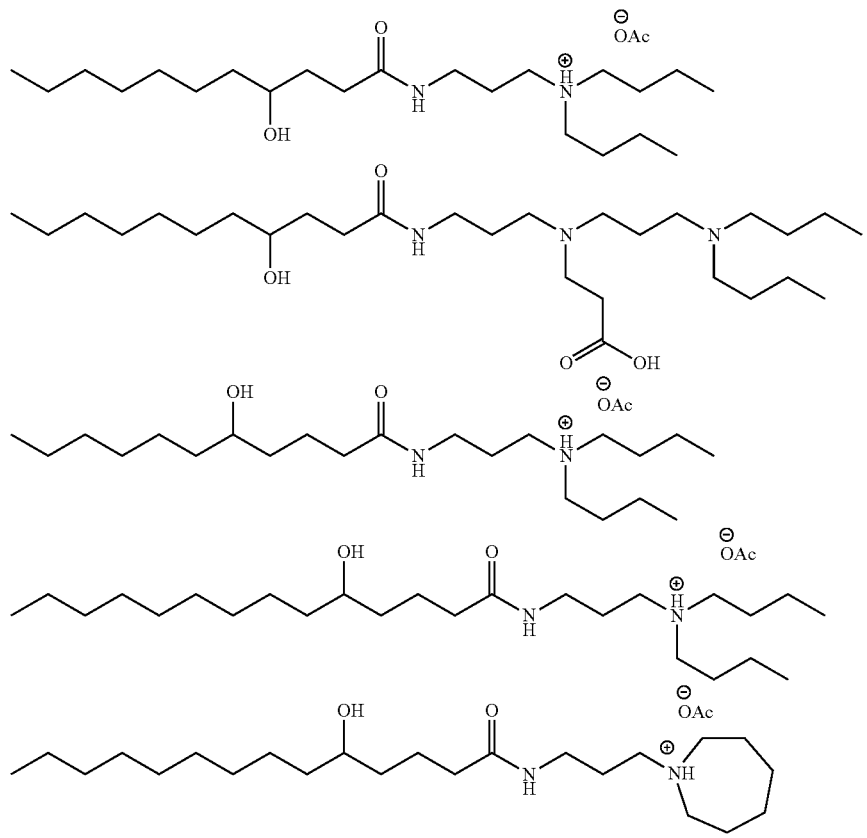

Embodiment 8: The composition as in one of embodiments 1-4, wherein the alcohol is an amino alcohol.

Embodiment 9: The composition as in one of embodiments 1-8, wherein the alkyl lactone-derived hydroxyamide or alkyl lactone-derived hydroxyester is from about 1 wt/v % to about 80 wt/v % based on the composition.

Embodiment 10: The composition as in one of embodiments 1-9, wherein the composition further comprises one or more thermodynamic gas hydrate inhibitors, kinetic gas hydrate inhibitors, anti-agglomerants, asphaltene inhibitors, paraffin inhibitors, scale inhibitors, emulsifiers, water clarifiers, dispersants, emulsion breakers, or any combination thereof.

Embodiment 11: The composition as in one of embodiments 1-10, wherein the alkyl lactone-derived hydroxyamide or alkyl lactone-derived hydroxyester comprises a reduced toxicity compared to compositions not containing alkyl lactone derived hydroxyamide or alkyl lactone-derived hydroxyester.

Embodiment 12: The composition as in one of embodiments 1-11, wherein the alkyl lactone-derived hydroxyamide or alkyl lactone-derived hydroxyester comprises a 48-hour $EC_{50}$ value with Daphnia magna greater than or equal to 10 mg/ml.

Embodiment 13: The composition as in one of embodiments 1-12, wherein the alkyl lactone-derived hydroxyamide or alkyl lactone-derived hydroxyester comprises a 48-hour $EC_{50}$ value with Daphnia magna from about 10-100 mg/ml.

Embodiment 14: The composition as in one of embodiments 1-13, wherein the alkyl lactone-derived hydroxyamide or alkyl lactone-derived hydroxyester has an increased biodegradation compared to compositions not containing alkyl lactone derived hydroxyamide or alkyl lactone-derived hydroxyester.

Embodiment 15: The composition as in one of embodiments 1-14, wherein the alkyl lactone-derived hydroxyamide or alkyl lactone-derived hydroxyester has biodegradation of greater than 10%, greater than 20%, greater than 30%, greater than 40%, greater than 50% or greater than 60% when measured in a 28 day degradation test.

Embodiment 16: A composition comprising:
a fluid; and
the alkyl lactone-derived hydroxyamide or alkyl lactone-derived hydroxyester
composition as in one of embodiments 1-15.

Embodiment 17: The composition of claim 16, wherein the alkyl lactone-derived hydroxyamide or alkyl lactone-derived hydroxyester is about is about 1000 ppm to 50,000 ppm.

Embodiment 18: The composition as in one of embodiments 16-17, wherein the fluid comprises water, natural gas, and liquid hydrocarbon.

Embodiment 19: A composition comprising an alkyl lactone-derived hydroxyamide or alkyl lactone-derived hydroxyester having the general formula:

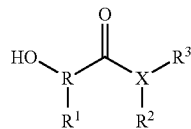

wherein X=nitrogen or oxygen;
wherein $R^1$=any fatty tail derived from 1-30 carbon saturated or unsaturated alkyl group or a ring structure including cyclohexyl, cyclopentyl, phenyl, benzyl, or variants thereof;
wherein $R^2$=is H or any 1-10 carbon saturated or unsaturated alkyl group or a ring structure which would link to $R^3$; and
wherein $R^3$=H or any 1-10 carbon saturated or unsaturated alkyl group or a ring structure which would link to $R^2$.

Embodiment 20: The composition of claim 19, wherein the alkyl lactone-derived hydroxyamide is:

amide formed by a reaction between an alkyl lactone with an amine, and the at least one alkyl lactone-derived hydroxyester formed by a reaction between an alkyl lactone with an alcohol.

Embodiment 22: The method of claim 21, wherein introducing is by injecting or pumping.

Embodiment 23: The method as in one of embodiments 21-22, wherein introducing is into a downhole.

Embodiment 24: The method as in one of embodiments 21-23, wherein the fluid is contained in an oil or natural gas production operation or pipeline.

Embodiment 25: The method as in one of embodiments 21-24, wherein the fluid comprises water, natural gas, and liquid hydrocarbon.

Embodiment 26: The method as in one of embodiments 21-25, wherein the fluid comprises water of about 1% to about 80% weight/weight with respect to a hydrocarbon phase.

Embodiment 27: The method as in one of embodiments 21-26, wherein the composition further comprises one or more thermodynamic gas hydrate inhibitors, kinetic gas hydrate inhibitors, anti-agglomerants, asphaltene inhibitors, paraffin inhibitors, scale inhibitors, emulsifiers, water clarifiers, dispersants, emulsion breakers, or any combination thereof.

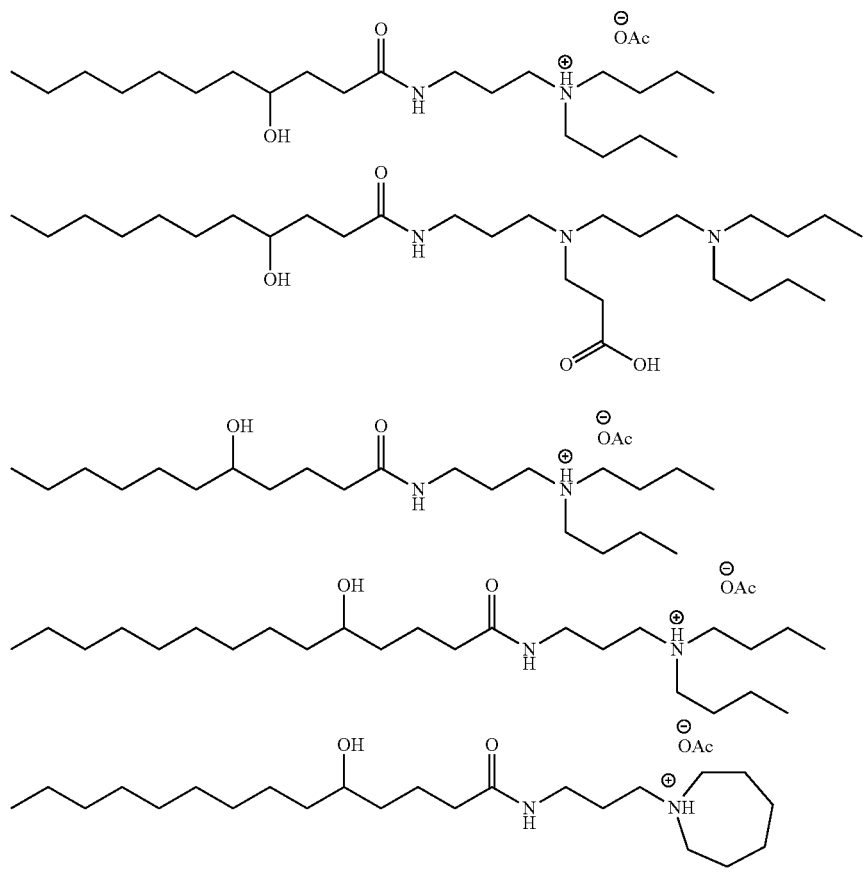

Embodiment 21: A method of inhibiting formation of agglomerates of natural gas hydrates comprising: introducing into a fluid a composition comprising at least one alkyl lactone-derived hydroxyamide or alkyl lactone-derived hydroxyester to inhibit formation of agglomerates of natural gas hydrates, the at least one alkyl lactone-derived hydroxy- Embodiment 28: The method as in one of embodiments 21-27, wherein the alkyl lactone comprises 2 to 30 carbon atom-containing lactone.

Embodiment 29: The method as in one of embodiments 21-28, wherein the alkyl lactone comprises 1 to 30 carbon atom-containing alkyl substituent.

Embodiment 30: The method as in one of embodiments 21-29, wherein the alkyl lactone comprises a decalactone or an undecalactone.

Embodiment 31: The method as in one of embodiments 21-30, wherein the amine comprises primary, secondary or tertiary amine.

Embodiment 32: The method as in one of embodiments 21-31, wherein the amine comprises a dibutylaminopropylenediamine, a dibutylaminopropylenediamine with an additional aminopropylamino moiety, or combination thereof.

Embodiment 33: The method as in one of embodiments 21-30, wherein the alcohol is an amino alcohol.

Embodiment 34: The method as in one of embodiments 21-33, wherein the alkyl lactone-derived hydroxyamide or alkyl lactone-derived hydroxyester has the general formula:

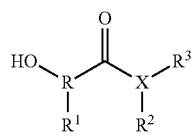

wherein X=nitrogen or oxygen;
wherein $R^1$=any fatty tail derived from 1-30 carbon saturated or unsaturated alkyl group or a ring structure including cyclohexyl, cyclopentyl, phenyl, benzyl, or variants thereof;
wherein $R^2$=is H or any 1-10 carbon saturated or unsaturated alkyl group or a ring structure which would link to $R^3$; and
wherein $R^3$=H or any 1-10 carbon saturated or unsaturated alkyl group or a ring structure which would link to $R^2$.

Embodiment 35: The method as in one of embodiments 21-34, wherein, the alkyl lactone-derived hydroxyamide comprises:

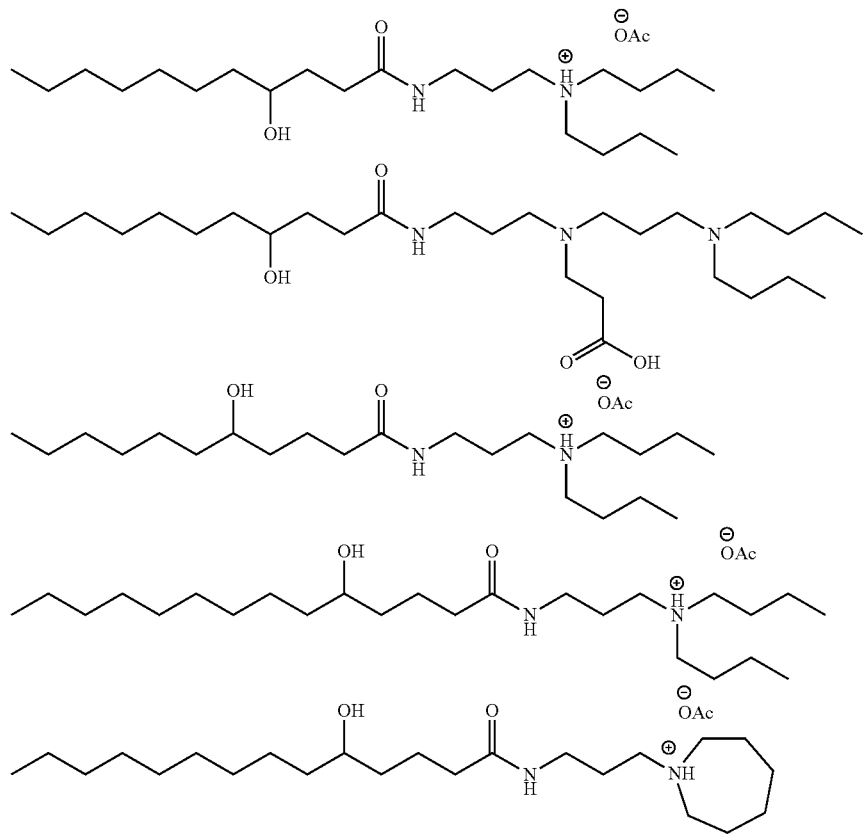

Embodiment 36: Use of the alkyl lactone-derived hydroxyamide or alkyl lactone-derived hydroxyester as in one of embodiments 1-35 to inhibit agglomerates of natural gas hydrates.

EXAMPLES

The following examples are intended to illustrate different aspects and embodiments of the invention and are not to be considered limiting the scope of the invention. It will be recognized that various modifications and changes may be made without following the experimental embodiments described herein, and without departing from the scope of the claims.

Example 1

γ-undecalactone/DBAPA

In a 250 mL round bottom 2-necked flask was weighed 60.0 g of dibutylaminopropylamine and 59.28 g of γ-undecalactone (1.0 eq). The flask was equipped with stir bar and set to stir at 60° C. for 6 hours with a nitrogen blanket. The flask contents were cooled to room temperature and treated with 22.1 mL of glacial acetic acid (1.0 eq), then diluted to 50 wt % active in methanol.

δ-undecalactone/DBAPA

In a 20 mL, Teflon top vial was weighed 5.0 g of δ-undecalactone and 4.94 g of dibutylaminopropylamine (1 eq). A stir bar was added and the vial was set to stir at 40° C. for 2 hours. A thickening of the contents was observed, and the temperature of the vial was increased to 70° C. and allowed to stir for 24 hours. The contents were allowed to return to room temperature and 0.972 g acetic acid (1.0 eq) was added. Finally, the contents were diluted to 50 wt % active in xylene.

δ-tetradecalactone/DBAPA

In a 20 mL, Teflon top vial was weighed 2.0 g of δ-tetradecalactone and 1.38 g of dibutylaminopropylamine (1 eq). A stir bar was added and the flask was set to stir at 60° C. for 20 minutes. A thickening of the contents was observed and the reaction was halted. The contents were allowed to return to room temperature and 0.53 g acetic acid (1.0 eq) was added. Finally, the contents were diluted to 50 wt % active in 9:1 methanol:xylene.

Example 2

The rocking cell test was used to determine if the alkyl lactone-derived hydroxyamide compounds described in Example 1 were able to minimize gas hydrate agglomerant particles and disperse those particles into a hydrocarbon phase.

The rocking cell includes a rack on which individual cells are placed. Each individual cell includes a sapphire tubing containing a stainless steel ball inside the sapphire tubing. The stainless steel ball induces turbulence and mixes the liquids during the rocking process. The sapphire tubing can also withstand pressures up to about 5,000 psi. Once the cells are mounted onto the rack, the rack rocks up and down slowly, at a rate of about 1 complete cycle (up and down) per minute. The rack was further contained within a temperature controlled bath attached to a chiller.

The compositions include a hydrocarbon, an aqueous phase, a gas and the alkyl lactone-derived hydroxyamide to be tested. The aqueous phase used was a brine of about 4% salinity and a water content of 25% of the composition. Various crude oils such as black oil, heavy black oil and condensate were tested. WDDM synthetic gas (~85% methane synthetic blend, which is a Type II gas hydrate forming gas blend) was used to pressurize the cells at the appropriate pressure. 2500 psi for the black oil and heavy black oil conditions, and 2000 psi for condensate.

Injected first into each cell was the brine and the gas. The alkyl lactone-derived hydroxyamide was then dosed according to the amount of the brine in the test cell. The crude oil was heated to 60° C. for a minimum of 2 hours prior, then introduced into the cell containing the brine, gas, and the alkyl lactone-derived hydroxyamide.

The cells with the test compositions were then equilibrated to a temperature of about 29° C., while rocking for 30 minutes.

The test is a constant pressure test where the cells are left open to a booster that boosts additional gas into the cells as gas was solubilized into the liquids and/or formed gas hydrates. The cells were rocked for about 30 minutes to equilibrate and mix prior to stopping at a horizontal position (shut-in). In the shut-in phase, the cells were cooled down to about 4.4° C. over approximately four hours and when the cells reached 4.4° C., they were rocked for an additional eight hours at 4.4° C. After a shut-in time of about 8 hours, the rocking of the cells was restarted for two hours. After two hours the cells were visually observed and ranked as pass/fail.

The pass/fail criteria were based on the ability of the ball in the rocking cell to move within the sapphire tube. For example, an alkyl lactone-derived hydroxyamide tested was considered effective and passed the rocking cell test if at the time of the ranking, the ball moved freely when the cell was rocked indicating that few agglomerates were formed. In contrast, the alkyl lactone-derived hydroxyamide failed if the ball's movement was obstructed or completely stopped by the formation of gas hydrate agglomerates. The anti-agglomerate's performance was considered borderline when there was observable gas hydrate agglomerates and at least some of the agglomerates stuck to the walls of the sapphire tube; when these agglomerates were present and the movement of the ball was not restricted, the alkyl lactone-derived hydroxyamide ranking was considered borderline pass.

FIG. 1 shows the results as passing the rocking cell test when tested with an alkyl lactone-derived hydroxyamide (which is a reaction product with γ-undecalactone and dibutylaminopropylamine) dosed at 3% with 25% water cut and 4% salinity in black oil.

Figure 2:
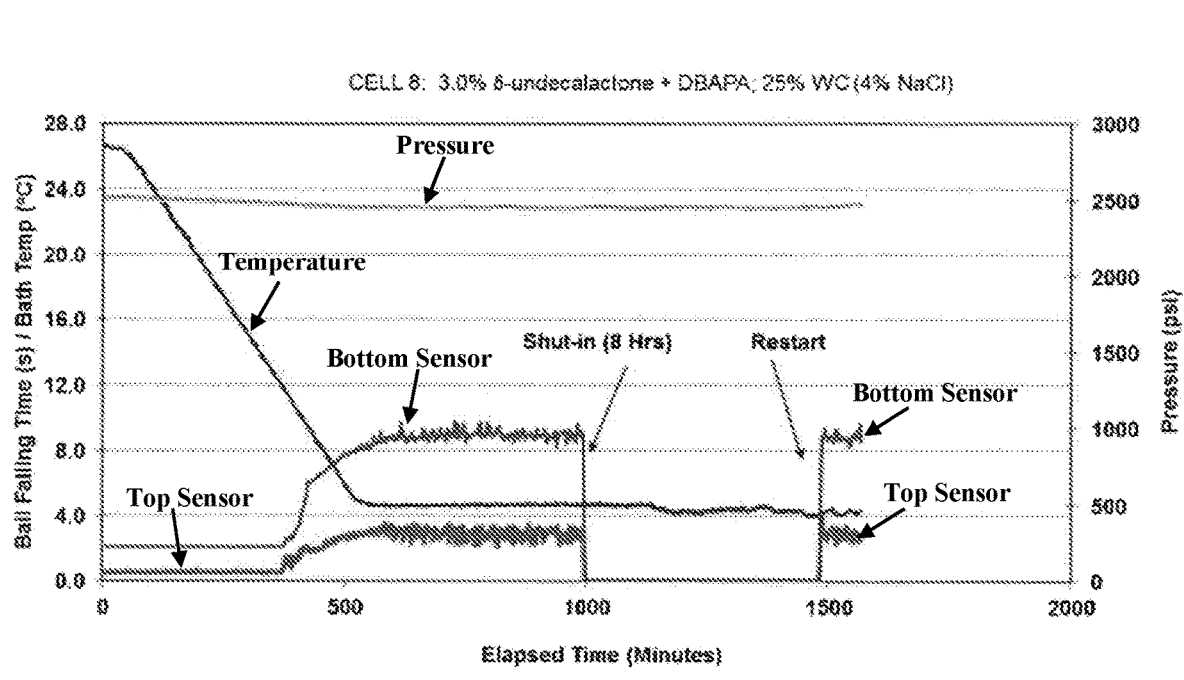
FIG. 2 is a graphical representation of cell pressure as a function of run time for a formulation of an embodiment of the invention.

FIG. 2 shows the results as passing the rocking cell test when the alkyl lactone-derived hydroxyamide tested (reaction between δ-undecalactone and dibutylaminopropylamine) dosed at 3% with 25% water cut and 4% salinity in black oil.

Figure 3:
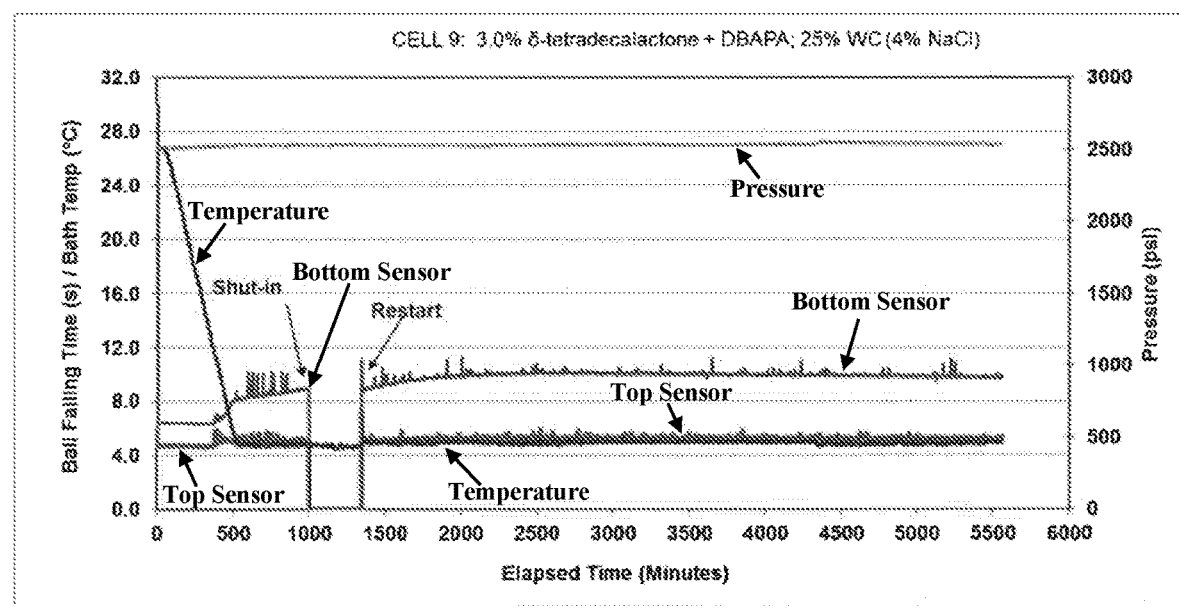
FIG. 3 is a graphical representation of cell pressure as a function of run time for a formulation of an embodiment of the invention.

FIG. 3 shows the results as passing the rocking cell test when the alkyl lactone-derived hydroxyamide tested (reaction between δ-tetradecalactone and dibutylaminopropylamine) dosed at 3% with 25% water cut and 4% salinity in black oil.

Figure 4:
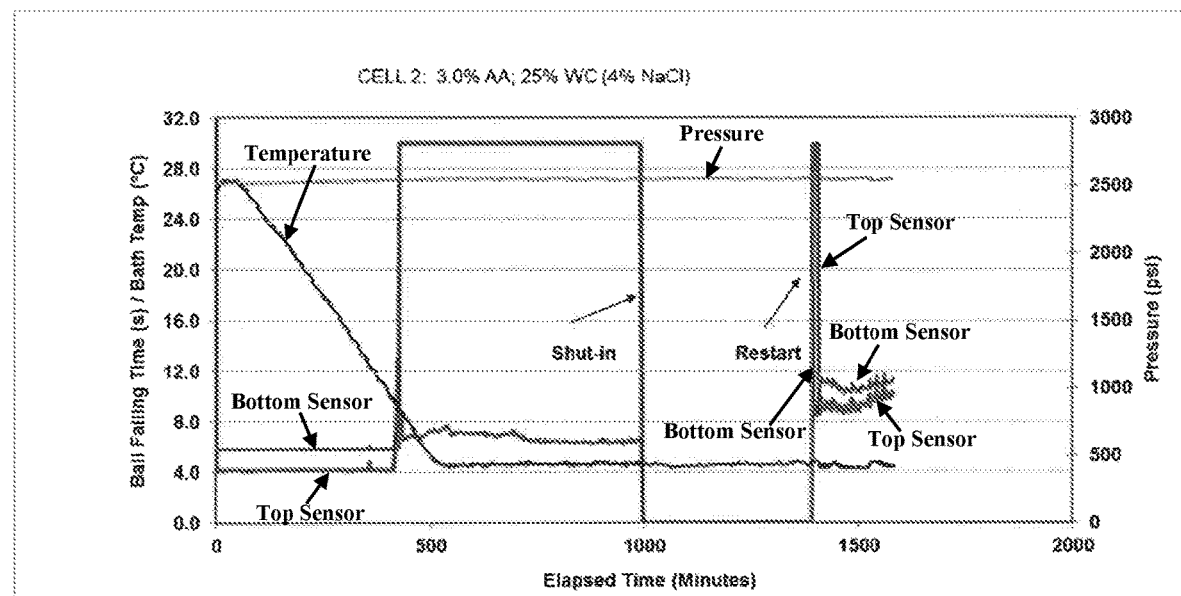
FIG. 4 is a graphical representation of cell pressure as a function of run time for a formulation of an embodiment of the invention.

FIG. 4 shows that the results with γ-undecalactone/DBAPA dosed at 3% with 25% water cut and 4% salinity in black oil. The results show that the alkyl lactone-derived hydroxyamide or alkyl lactone-derived hydroxyester failed the criteria as indicated by the maximized ball fall time (red trace) indicating a blockage on the side of the cell.

Figure 5:
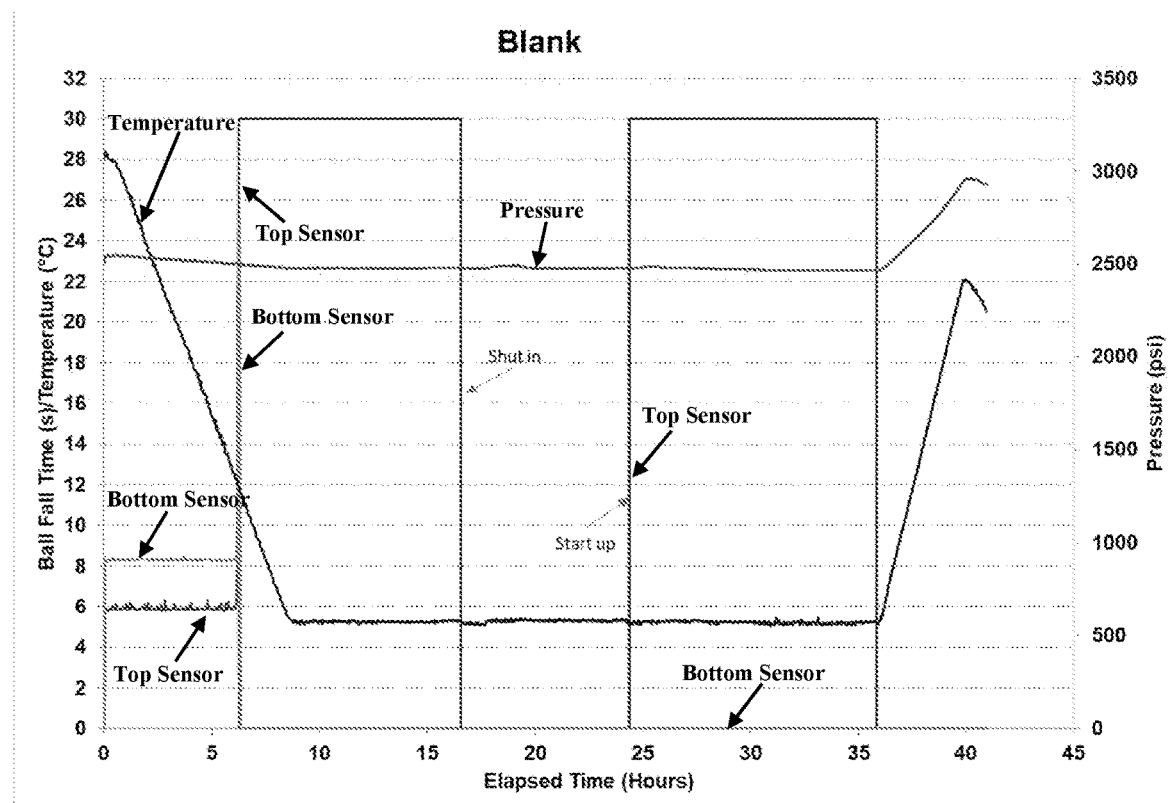
FIG. 5 is a graphical representation of cell pressure as a function of run time for a blank formulation.

FIG. 5 shows a blank with 25% water cut and 4% salinity in black oil. The results show that the system fails upon cool down as indicated by the maximized ball fall time (red trace) indicating a blockage on the side of the cell.

What is claimed is:

1. A composition comprising an alkyl lactone-derived hydroxyamide, wherein the alkyl lactone-derived hydroxyamide is a reaction product of an alkyl lactone and an amine, wherein the alkyl lactone-derived hydroxyamide comprises:

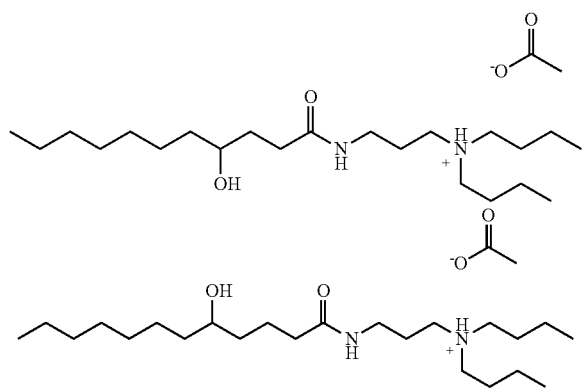

-continued

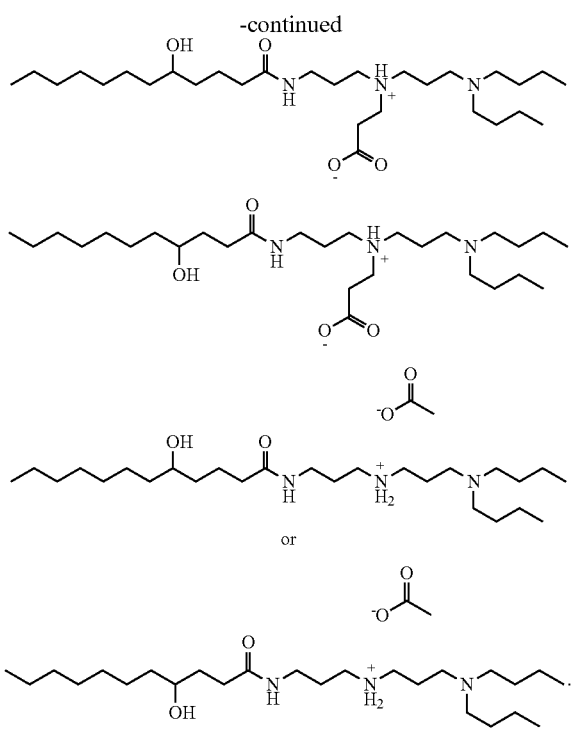

2. The composition of claim 1, wherein the composition further comprises one or more thermodynamic gas hydrate inhibitors, kinetic gas hydrate inhibitors, anti-agglomerants, asphaltene inhibitors, paraffin inhibitors, scale inhibitors, emulsifiers, water clarifiers, dispersants, emulsion breakers, or any combination thereof.

3. The composition of claim 1, wherein the alkyl lactone-derived hydroxyamide comprises a 48-hour $EC_{50}$ value with Daphnia magna greater than or equal to 10 mg/ml.

4. The composition of claim 1, wherein the alkyl lactone-derived hydroxyamide has biodegradation of greater than 10%, greater than 20%, greater than 30%, greater than 40%, greater than 50% or greater than 60% when measured in a 28 day degradation test.

5. The composition of claim 1, further comprising:
a fluid comprising water, natural gas, and liquid hydrocarbon.

6. The composition of claim 5, wherein the fluid comprises water in a range of from about 1 wt % to about 80 wt % based on a weight of the liquid hydrocarbon.

7. The composition of claim 5, wherein the alkyl lactone-derived hydroxyamide is present in a range of from about 1,000 ppm to about 50,000 ppm based on a total weight of the composition.

* * * * *